United States Patent [19]
Yamamoto

[11] Patent Number: 5,091,588
[45] Date of Patent: Feb. 25, 1992

[54] FLUORINATED STYRENE DERIVATIVES AND METHOD FOR MAKING

[75] Inventor: Yasushi Yamamoto, Takasaki, Japan

[73] Assignee: Shin-Etsu Chemical Co., Ltd., Tokyo, Japan

[21] Appl. No.: 584,752

[22] Filed: Sep. 19, 1990

[30] Foreign Application Priority Data

Sep. 26, 1989 [JP] Japan .................. 1-249743

[51] Int. Cl.$^5$ .......................... C07C 43/166
[52] U.S. Cl. .................................. 568/607
[58] Field of Search ............ 568/662, 663, 607

[56] References Cited

FOREIGN PATENT DOCUMENTS 1293943 12/1986 Japan .................. 568/633

Primary Examiner—Marianne Cintins
Assistant Examiner—Margaret Argo
Attorney, Agent, or Firm—Birch, Stewart, Kolasch & Birch

[57] ABSTRACT

Fluorinated styrene derivatives of the general formula:

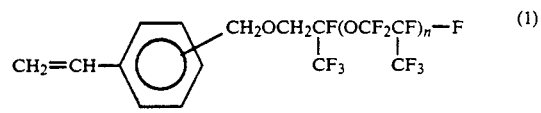

wherein n is an integer of 1 to 3 are novel. They form homopolymers and copolymers having water and oil repellency, chemical resistance and flexibility. They are prepared by reacting a halomethylstyrene with an alcohol having a perfluoropolyether group in the presence of a base.

7 Claims, 2 Drawing Sheets

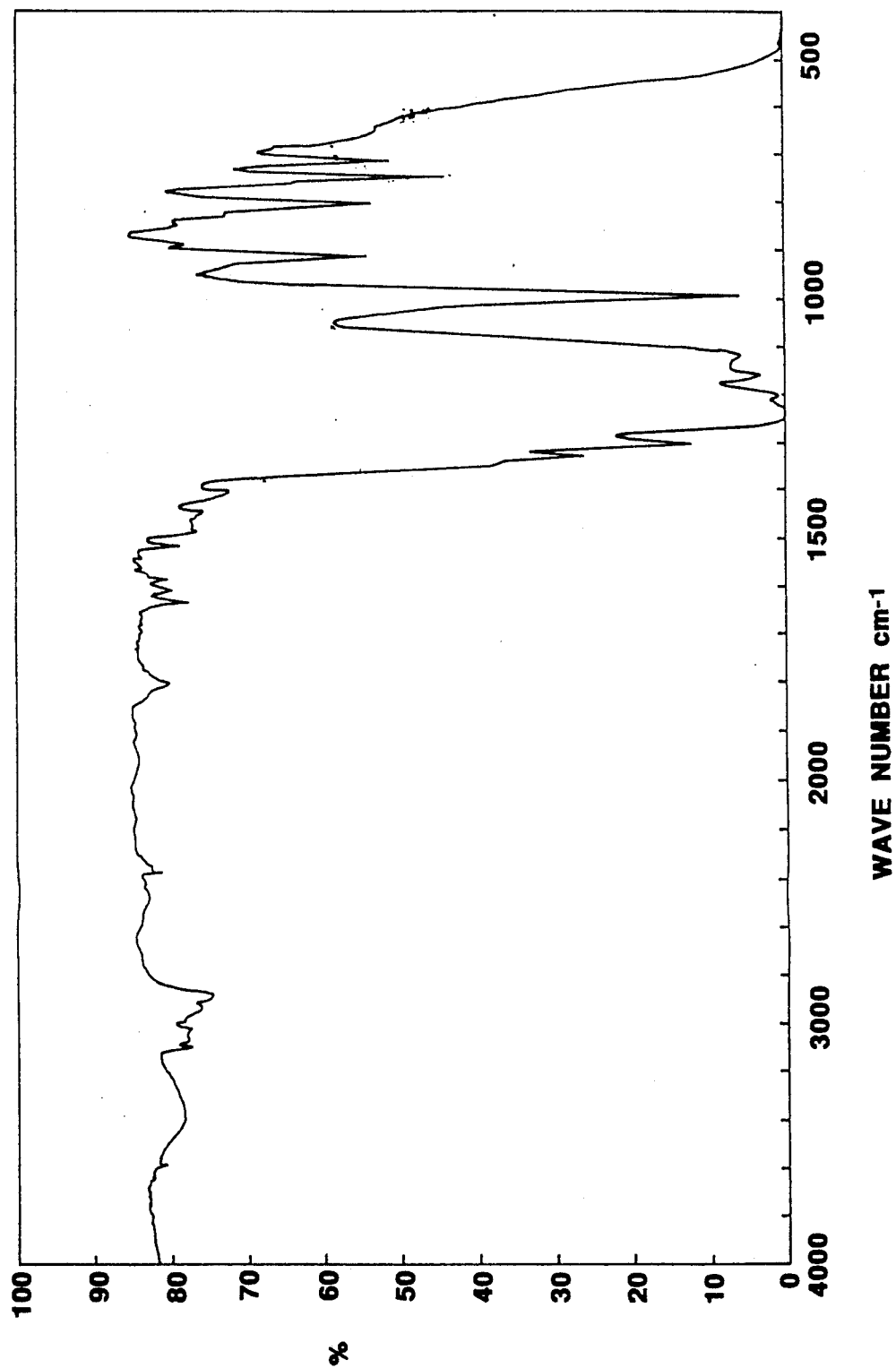

FLUORINATED STYRENE DERIVATIVES AND METHOD FOR MAKING

This invention relates to novel fluorinated styrene derivatives and a method for preparing the same.

BACKGROUND OF THE INVENTION

Styrene derivatives having a fluorinated organic group substituted at the para position are known in the art, for example, benzyl ethers of the general formula:

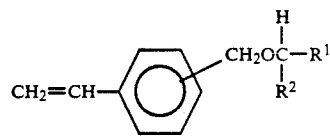

wherein $R^1$ and $R^2$ are polyfluoroalkyl groups as disclosed in Japanese Patent Application Kokai No. 293943/1986. Introduction of such a polyfluoroalkyl group into the substituent moiety of styrene can impart water repellency, oil repellency and chemical resistance attributable to fluorine to a homopolymer of the styrene or a copolymer of the styrene with another polymerizable monomer at the sacrifice of flexibility. It is thus desired to overcome the drawback that the resulting polymers are brittle.

SUMMARY OF THE INVENTION

Therefore, an object of the present invention is to provide a novel and improved styrene derivative which can impart water repellency, oil repellency and chemical resistance to polymers thereof while maintaining flexibility. Another object is to provide a method for preparing such a styrene derivative.

The inventors have found that the polyfluoroalkyl groups introduced as a fluorinated organic group into the prior art styrene derivatives are stiff enough to eliminate flexibility from the resulting polymers or to render the polymers brittle, and that use of a more flexible perfluoroether group as the fluorinated organic group makes it possible to impart the attributes of fluorine while maintaining softness.

According to the present invention, there is provided a novel fluorinated styrene derivative of the general formula:

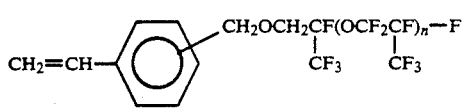

wherein n is an integer of 1 to 3.

The present invention also provides a method for preparing a fluorinated styrene derivative of formula (1), comprising the step of:

reacting a styrene derivative of the general formula:

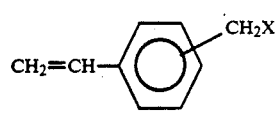

wherein X is a halogen atom with a fluorinated alcohol of the general formula:

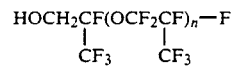

wherein n is as defined above.

The fluorinated styrene derivatives of formula (1) can be polymerized alone or with another polymerizable monomer to form a homopolymer or copolymer which has excellent water repellency, oil repellency and chemical resistance as well as flexibility. These polymers are useful in forming coatings and gas separating membranes.

BRIEF DESCRIPTION OF THE DRAWINGS

FIGS. 1 and 2 are charts showing IR spectra of the end products obtained in Examples 1 and 2.

DETAILED DESCRIPTION OF THE INVENTION

Figure 1:
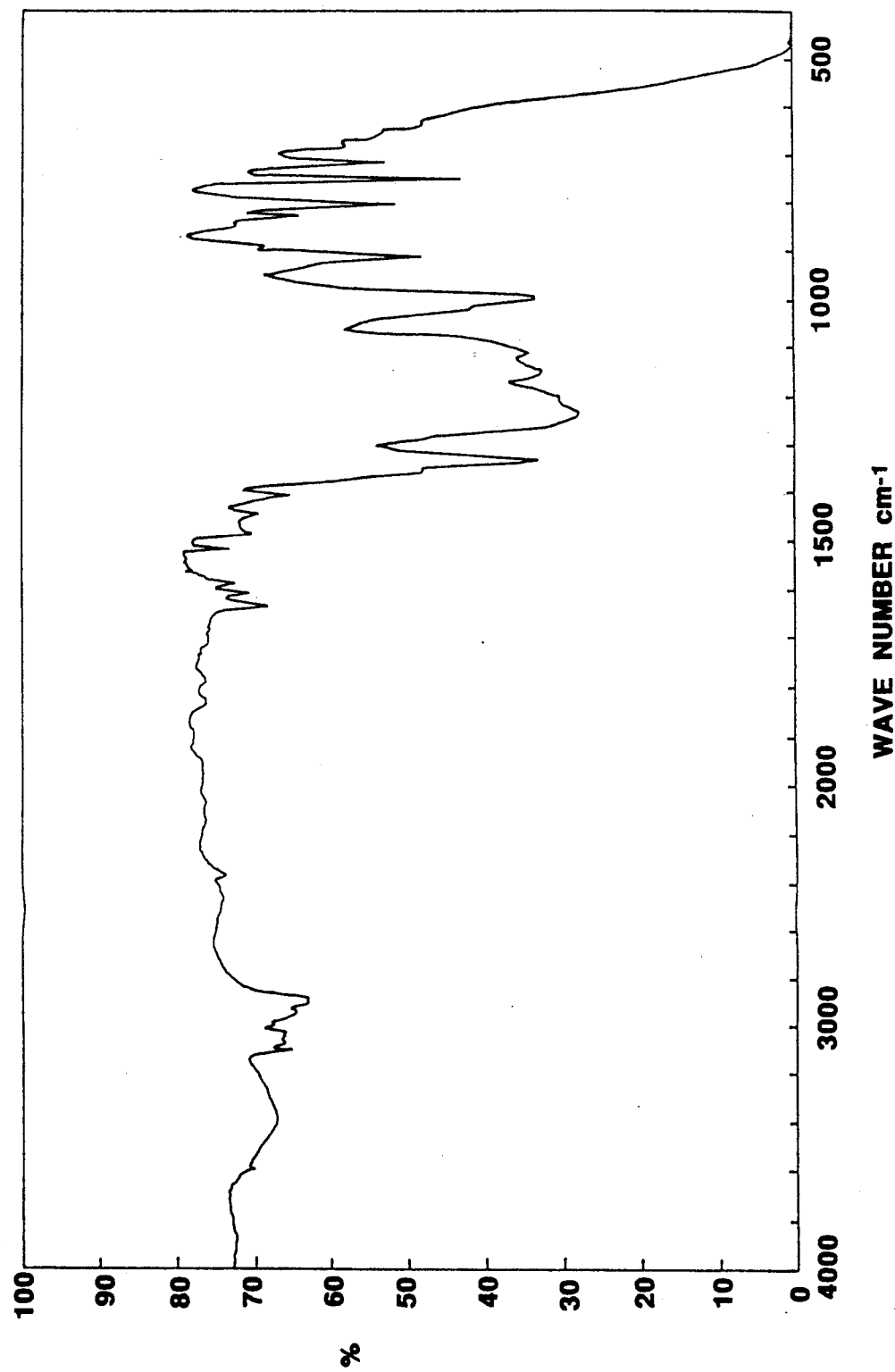

The fluorinated styrene derivatives of the present invention are of the following general formula.

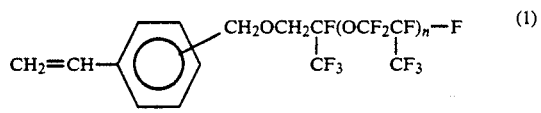

They are synthesized, for example, by reacting a halomethylstyrene, that is, a styrene derivative of the general formula:

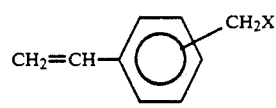

wherein X is a halogen atom such as chlorine and bromine with an alcohol having a perfluoropolyether group, that is, a fluorinated alcohol of the general formula:

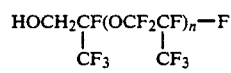

wherein n is as defined above in the presence of a base. Often, 1 mol of the halomethylstyrene of formula (2) is reacted with 0.8 to 2 mol, preferably 1 to 1.5 mol of the alcohol of formula (3).

The halomethylstyrene derivatives of formula (2) include p-chloromethylstyrene, m-chloromethylstyrene, and p-bromomethylstyrene.

The alcohols having a perfluoropolyether group of formula (3) may be synthesized by well-known methods according to the following reaction scheme.

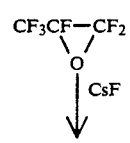

-continued

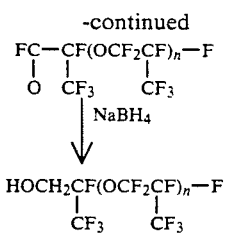

Letter n is an integer of 1 to 3. If n is more than 3, the perfluoropolyether group is too long to purify the end derivative by distillation and the attributes of fluorine are not fully imparted to the resulting polymer.

The bases which can be used in the reaction between the compounds of formulae (2) and (3) include alkali metal hydroxides such as sodium hydroxide and potassium hydroxide, alkali metal hydrides such as sodium hydride and potassium hydride, and alkali metal alkoxides such as sodium methoxide, potassium methoxide, sodium ethoxide, and potassium tertiary butoxide. The amount of the base used generally ranges from 1.0 to 2.5 mol, preferably 1.2 to 1.5 mol per mol of halogen in halomethylstyrene. Usually, the use of alkali metal hydrides and alkoxides is limited to anhydrous polar solvent systems (Williamson reaction) although alkali metal alkoxides may be used in aqueous systems without a further benefit.

The reaction between the compounds of formulae (2) and (3) may be conducted in a polar solvent, but preferably in a two phase system of organic and aqueous phases. The organic phase-forming solvents include benzene, toluene, diethyl ether, cyclohexane, $\alpha,\alpha,\alpha,\alpha'$-,$\alpha',\alpha'$-hexafluoro-p-xylene, and $\alpha,\alpha,\alpha,\alpha',\alpha',\alpha'$-hexafluoro-m-xylene. Upon reaction, a phase transfer catalyst such as tetrabutylammonium hydrogen sulfate may be used.

The reaction temperature generally ranges from 0° to 130° C., preferably from 10° to 80° C. Most preferably reaction is conducted at a temperature of lower than 60° C. in the presence of a polymerization inhibitor in order to prevent polymerization of the reactants and products. The polymerization inhibitors used herein are those commonly used for styrene derivatives, for example, phenolic polymerization inhibitors such as p-methoxyphenol, 4-methyl-2,6-di-t-butylphenol, and 2,2'-methylenebis(4-ethyl-6-t-butylphenol), and carbamate polymerization inhibitors such as copper dimethyldithiocarbamate alone and mixtures thereof. The inhibitor is generally used in an amount of 500 to 5,000 ppm, typically 1,000 to 2,000 ppm based on the halomethylstyrene. The progress of reaction is traced by gas chromatography and considered complete when one reactant, typically the halogenated methylstyrene disappeared. The reaction time is usually from about 5 to about 30 hours.

The fluorinated styrene derivative of formula (1) can be polymerized alone or with another polymerizable monomer to form a homopolymer or a copolymer which exhibits water repellency, oil repellency and chemical resistance attributable to fluorine as well as flexibility.

EXAMPLE

Examples of the present invention are given below by way of illustration and not by way of limitation.

EXAMPLE 1

A four-necked flask was charged with 32 grams (0.8 mol) of sodium hydroxide and 74 grams of water. With stirring and water cooling, 205 grams (0.65 mol) of 2-trifluoromethyl-2,4,4,5,5,6,6,6-octafluoro-3-oxahexanol was added dropwise over 15 minutes. At the end of addition, there were added 34 grams of tetra-n-butylammonium hydrogen sulfate, 0.1 gram of 2,2'-methylenebis(4-ethyl-6-t-butylphenol), 0.1 gram of copper dimethyldithiocarbamate, and 100 ml of $\alpha,\alpha,\alpha,\alpha',\alpha',\alpha'$-hexafluoro-m-xylene. Then 92 grams (0.6 mol) of p-chloromethylstyrene was added dropwise over one hour while the reaction mixture was maintained below 30° C. At the end of addition, the reaction mixture was stirred for 2 hours at 50° to 60° C. and then for one day at room temperature.

After water treatment, the organic layer was taken out and dried over sodium sulfate. After the hexafluoro-m-xylene was removed in vacuum, vacuum distillation was continued to yield as a fraction at 72°-73° C. and $7.6 \times 10^{-5}$ mmHg 186 grams (yield 72%) of p-(4-trifluoromethyl-4,6,6,7,7,8,8,8-octafluoro-2,5-dioxaoctyl)styrene.

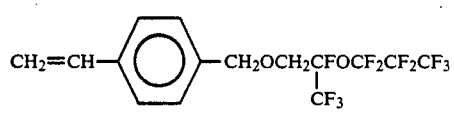

The elemental analysis, molecular weight, nuclear magnetic resonance (NMR) spectrum, and infrared (IR) absorption spectrum of this compound are shown below.

| Elemental analysis: | C | H |
|---|---|---|
| Calcd. for $C_{15}H_{11}F_{11}O_2$ | 41.7% | 2.6% |
| Found | 42.0% | 2.7% |

Molecular weight (mass spectrum): 432

| NMR spectrum: δ value (ppm) (CCl₄ 60% internal standard TMS) | |
|---|---|
| 3.77, 3.97 | (d, 2H, —OC$\underline{H}_2$—CF) |
| 4.48 | 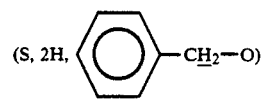 (S, 2H, —C$\underline{H}_2$—O) |
| 4.98–5.87 | (m, 2H, C$\underline{H}_2$=C) |
| 6.30–7.10 | 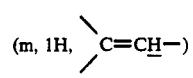 (m, 1H, C=C$\underline{H}$—) |
| 6.93–7.50 | (m, 4H, aromatic hydrogen) |

IR spectrum: 1590, 1610, 1635 cm$^{-1}$ (styryl group) 1110–1300 cm$^{-1}$ (C-F absorption)
The IR spectrum chart is shown in FIG. 1.

EXAMPLE 2

As in Example 1, 96.4 grams (0.2 mol) of 2,5-bis-trifluoromethyl-2,4,4,5,7,7,8,8,9,9,9-undecafluoro-3,6- dioxanonanol was reacted with 30.6 grams (0.2 mol) of p-chloromethylstyrene, yielding as a fraction at 96°-97° C. and $1.4 \times 10^{-4}$ mmHg 84 grams (yield 70%) of p-(4,7-bistrifluoromethyl-4,6,6,7,9,9,10,10,11,11,11-undecafluoro-2,5,8-trioxaundecyl)styrene.

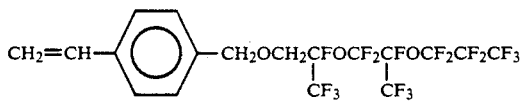

The elemental analysis, molecular weight, nuclear magnetic resonance (NMR) spectrum, and infrared (IR) absorption spectrum of this compound are shown below.

| Elemental analysis: | | |
| --- | --- | --- |
| | C | H |
| Calcd. for $C_{18}H_{11}F_{17}O_3$ | 36.1% | 1.9% |
| Found | 36.0% | 1.9% |

Molecular weight (mass spectrum): 598

| NMR spectrum: δ value (ppm) | |
| --- | --- |
| (CCl$_4$ 60% internal standard TMS) | |
| 3.77, 3.97 | (d, 2H, $-O\underline{C}H_2-CF$) |
| 4.43 | (S, 2H, 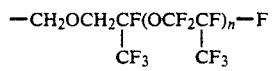$-CH_2-O$) |
| 4.97-5.87 | (m, 2H, $C\underline{H}_2=C$) |
| 6.30-7.13 | (m, 1H, $\diagdown C=C\underline{H}-$) |
| 6.90-7.07 | (m, 4H, aromatic hydrogen) |

IR spectrum: 1590, 1610, 1635 cm$^{-1}$ (styryl group)
1110-1300 cm$^{-1}$ (C-F absorption)

The IR spectrum chart is shown in FIG. 2.

Although some preferred embodiments have been described, many modifications and variations may be made thereto in the light of the above teachings. It is therefore to be understood that within the scope of the appended claims, the invention may be practiced otherwise than as specifically described.

I claim:

1. A fluorinated styrene derivative having the formula:

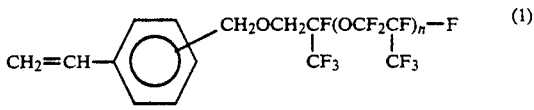

wherein n is an integer of 1 to 3.

2. The fluorinated styrene derivative as recited in claim 1 wherein n is 1.

3. The fluorinated styrene derivative as recited in claim 1 wherein n is 2.

4. The fluorinated styrene derivative as recited in claim 1 wherein n is 3.

5. A fluorinated styrene derivative as recited in claim 1, wherein the phenyl ring of the styrene moiety of Formula I is substituted at the para position by the $$-CH_2OCH_2CF(OCF_2CF)_n-F$$
$$\quad\quad\quad\quad\quad | \quad\quad\quad\quad |$$
$$\quad\quad\quad\quad\quad CF_3 \quad\quad\quad CF_3$$

group.

6. A fluorinated styrene derivative as recited in claim 5, which is p-(4-trifluoromethyl-4,6,6,7,7,8,8,8-octafluoro-2,5-dioxaoctyl)styrene.

7. A fluorinated styrene derivative as recited in claim 5, which is p-(4,7-bistrifluoromethyl-4,6,6,7,9,9,10,10,11,11,11-undecafluoro-2,5,8-trioxauncedyl)styrene.

* * * * *